(12) United States Patent
Bruder et al.

(10) Patent No.: US 6,600,803 B2
(45) Date of Patent: Jul. 29, 2003

(54) COMPUTED TOMOGRAPHY APPARATUS AND METHOD FOR OPERATING SAME

(75) Inventors: Herbert Bruder, Höchstadt (DE);
Heinrich Seifert, Bubenreuth (DE);
Horst Siebold, Effeltrich (DE)

(73) Assignee: Siemens Aktiengesellschaft, Munich (DE)

(*) Notice: Subject to any disclaimer, the term of this patent is extended or adjusted under 35 U.S.C. 154(b) by 99 days.

(21) Appl. No.: 09/968,152

(22) Filed: Oct. 1, 2001

(65) Prior Publication Data

US 2002/0071518 A1 Jun. 13, 2002

(30) Foreign Application Priority Data

Sep. 29, 2000 (DE) .......................................... 100 48 814

(51) Int. Cl.⁷ .................................................. H05G 1/60
(52) U.S. Cl. ............................................. 378/19; 378/4
(58) Field of Search ............................... 378/4, 19, 901; 382/131

(56) References Cited

U.S. PATENT DOCUMENTS

| | | | |
|---|---|---|---|
| 5,117,445 A | 5/1992 | Seppi et al. | 378/65 |
| 5,291,402 A | 3/1994 | Pfoh | 378/13 |
| 5,825,830 A | * 10/1998 | Kopf | 375/340 |

* cited by examiner

*Primary Examiner*—Drew A. Dunn
*Assistant Examiner*—Allen C. Ho
(74) *Attorney, Agent, or Firm*—Schiff Hardin & Waite

(57) ABSTRACT

In a computed tomography system equipped with a data-acquisition system and a method for operating such a computed tomography system, the computed tomography system has a radiation detector with at least one linear detector array composed of a row several detector elements aligned adjacent to one another. The data-acquisition system reads out the detector elements and forms difference signals from signals read out from pairs of adjacent detector elements.

16 Claims, 7 Drawing Sheets

COMPUTED TOMOGRAPHY APPARATUS AND METHOD FOR OPERATING SAME

BACKGROUND OF THE INVENTION

1. Field of the Invention

The present invention is directed to a computed tomography system equipped with a data-acquisition system, as well as a method for use with such a computed tomography system.

2. Description of the Prior Art

A computed tomography system of the type noted above has an X-ray source that directs a pyramidal X-ray beam through an object that is to be examined, e.g. a patient, onto a radiation detector. The X-ray source and, in some types of computed tomography systems, the radiation detector as well, are mounted on a gantry that can be rotated about the patient. The patient can be lying on a table that may be displaced or moved relative to the gantry along a system axis. This, inter alia, makes it possible to scan a portion of the patient's body in a spiral manner, so that a volume of the patient's body scanned. The values measured during the process are used to reconstruct sectional views of planar slices of the patient.

The radiation detector of the computed tomography system can have a linear detector array composed of a row of several detector elements aligned adjacent to one another or, as described, for example, in U.S. Pat. No. 5,291,402, several parallel linear detector arrays. The advantage of employing a computed tomography system equipped with a multi-line radiation detector is, for example, the ability to more rapidly scan a volume of the patient's body that is of interest, which, among other things, reduces the recording time. The disadvantage of employing a computed tomography system equipped with a multi-line radiation detector, however, is that it has a larger number of detector elements, which means that more detector elements must be read out during each scanning step than in the case of a computed tomography system equipped with a single-line radiation detector. This, in turn, leads to higher data rates for signals coming from a data-acquisition system that reads out the detector elements.

A radiological therapy device that has a photodiode array preceded by an X-ray image intensifier is known from U.S. Pat. No. 5,117,445. The photodiode array preceded by an X-ray image intensifier converts X-ray radiation into electrical signals. The electrical signals may be falsified, however, by geometric non-linearities of the X-ray image intensifier, which is why at least some of the output signals at the photodiode array must be interpolated in a suitable manner.

SUMMARY OF THE INVENTION

An object of the present invention to provide a computed tomography system of the type initially described with a data-acquisition system configured so that a prerequisite for lower data rates is satisfied. Another object of the invention is to specify a method for use with such a computed tomography system that will allow the data rates to be reduced.

The first object is achieved in accordance with invention in a computed tomography system equipped with a data-acquisition system and a radiation detector that has at least one linear detector array composed of several detector elements aligned up adjacent to one another, the data-acquisition system reading out the detector elements and forming and further processing difference signals from signals read out from pairs of adjacent detector elements. Since it is highly likely that any differences in the amplitudes of signals read out from pairs of adjacent detector elements will be slight, the rates of change of their difference signals will also be slight. Employing difference signals will thus allow data rates to be reduced compared to the conventional case where signals read out from single detector elements are employed. In a variant of the invention the data-acquisition system has at least one analog/digital converter that digitizes the signals read out from the detector elements. This advantageously makes it possible to form the difference signals at the digital level.

In an embodiment of the invention the data-acquisition system has at least one analog/digital converter that digitizes the difference signals read out from pairs of adjacent detector elements.

If, in an embodiment of the invention, the digitized difference signals have a data length of one byte, the data rates for a computed tomography system according to the invention will be low.

In a further embodiment of the invention the radiation detector is formed of several detector modules each composed of several linear detector arrays, which in turn each have several detector elements aligned adjacent to one another, and each of the detector modules is assigned an analog/digital converter.

The other object of the invention is achieved in a first embodiment of a method for acquiring signals from a computed tomography system equipped with a data-acquisition system and a radiation detector that has at least one detector module with at least one linear detector array with several detector elements aligned adjacent to one another, having the following method steps:

a.) reading out each detector element of a detector module at each scanning step and b.) forming signals $S^*_{j,m,k}$ from signals read out from detector elements of the $j^{th}$ detector module, where $$S^*_{j,m,1} = S_{j,m,1} \text{ for } k=1$$

and $$S^*_{j,m,k} = S_{j,m,k} - S_{j,m,k-1} \text{ for } 1 < k \leq K,$$

where $S_{j,m,k}$ is the signal read out from the $k^{th}$ detector element of the $m^{th}$ linear detector array of the $j^{th}$ detector module and K is the number of detector elements in the $m^{th}$ linear detector array.

As explained above, it is highly likely that signals read out from pairs of adjacent detector elements will have slight differences in amplitude. Since the rates of change of the difference signals will thus also be slight, employing the difference signals will allow data rates to be reduced compared to the conventional case where signals read out from single detector elements are employed.

According to the invention, the second object also is achieved in a second embodiment of a method for acquiring signals from a computed tomography system equipped with a data-acquisition system and a radiation detector that has at least one detector module with at least one detector column with several detector elements aligned adjacent to one another, having the following method steps:

a.) reading out each detector element of a detector module at each scanning step and b.) forming signals $S^*_{j,m,k}$ from signals read out from detector elements of the $j^{th}$ detector module, where $$S^*_{j,1,k} = S_{j,1,k} \text{ for } m=1$$

and $$S_{j,m,k} = S_{j,m,k} - S_{j,m-1,k} \text{ for } 1 < m \leq M,$$

where $S_{j,m,k}$ is the signal read out from the mth detector element of the $k^{th}$ detector column of the $j^{th}$ detector module and M is the number of detector elements in the $k^{th}$ detector column.

The reduced rates of change of the difference signals may thus be exploited in an advantageous manner for reducing the data rates.

In a variant of the invention, the signals $S_{j,m,k}$ are further processed in digital form in the method. It is thus advantageously possible to form the difference signals at the digital level.

In an embodiment of the invention, the signals $S^*_{j,m,k}$ are further processed in digital form in the method.

If, in a further embodiment of the method, the digital difference signals have a data length of one byte, data rates may be kept low in an advantageous manner.

DESCRIPTION OF THE PREFERRED EMBODIMENTS

Figure 1:
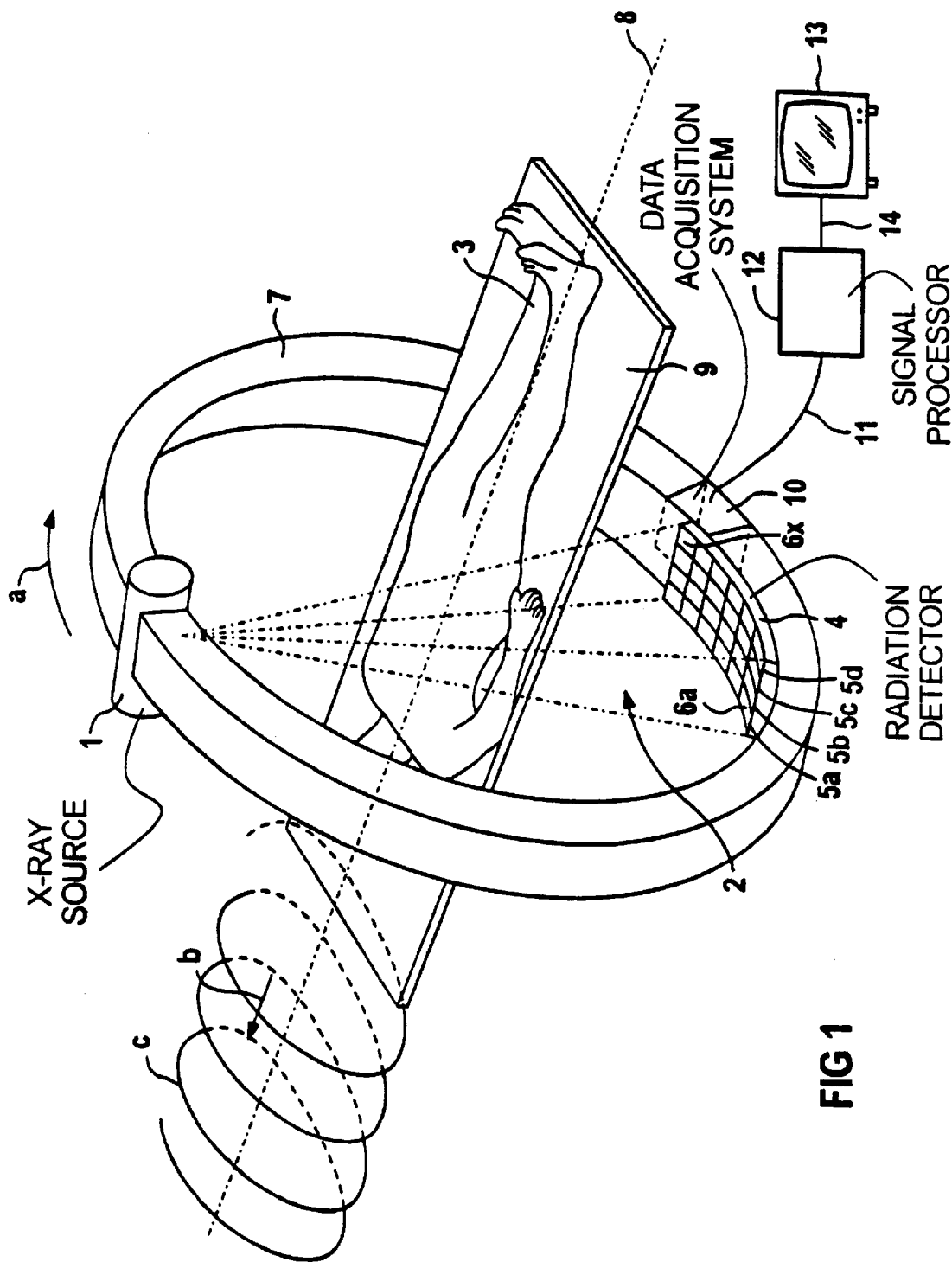
FIG. 1 shows a computed tomography system according to the invention.

FIG. 1 schematically depicts a computed tomography system according to the invention equipped with an X-ray source 1, emitting a pyramidal X-ray beam 2, whose marginal rays are represented by the dot-dashed lines in FIG. 1, that penetrates an object 3 to be examined, for example a patient, and that is incident on a radiation detector 4. In the exemplary embodiment, the radiation detector 4 has four linear detector arrays, 5a through 5d, adjacent to one another, with several detector elements, 6a through 6x, aligned adjacent to one another.

The X-ray source 1 and the radiation detector 4 are, in the exemplary embodiment, mounted opposite to one another on an annular gantry 7. The gantry 7 is mounted on a mounting fixture that is not shown in FIG. 1 such that it may be rotated (cf. arrow a) around a system axis 8 that passes through the center of the annular gantry 7.

In the exemplary embodiment, the patient 3 is lying on a table 9 that is transparent to X-rays and that is mounted such that it can be displaced (cf. arrow b) along the system axis 8 using a supporting mechanism that is not shown in FIG. 1.

The X-ray source 1 and the radiation detector 4 thus form a metrological system that can be rotated around the system axis 8 and displaced along the system axis 8 relative to the patient 3 so that the patient 3 can be X-rayed at various projection angles relative to said system axis 8 and at various positions along the system axis 8. The resultant output signals of the individual detector elements, 6a through 6x, are read out by a data-acquisition system 10 mounted on said gantry 7. The data-acquisition system 10 forms difference signals from adjacent detector elements 6a through 6x. The signals are sent to a signal processor 12, that computes an image of the patient 3 that, in turn, can be displayed on a monitor 13, by means of an electrical cable 11 that incorporates a slip-ring system, or a wireless transmission link in a manner that has not been illustrated. In the exemplary embodiment, the monitor 13 is connected to the signal processor 12 by an electrical cable 14.

The computed tomography system depicted in FIG. 1 can be employed for performing either sequential scans or spiral scans.

In the case of sequential scans, scanning of the patient 3 takes place in slices. The X-ray source 1 and the radiation detector 4 are rotated around the patient 3 relative to the system axis 8, and the measurement system formed by the X-ray source 1 and the radiation detector 4 records numerous projections in order to scan two-dimensional slices of the patient 3. Sectional views representing the scanned slices are reconstructed from the resultant measurement data. The patient 3 is in each case moved along the system axis 8 between scans of consecutive slices. This procedure is repeated until all slices of interest have been scanned.

During spiral scans, the measurement system formed by the X-ray source 1 and the radiation detector 4 is rotated around said system axis 8, and the table 9 is continuously moved in the direction of the arrow b, i.e., the measurement system is continuously moved along a spiral path c relative to the patient 3 until such time as the entire portion of the patient 3 that is of interest has been scanned, thereby generating a dataset representing a volume. The signal processor 12 computes planar data from which, as in the case of sequential scanning, sectional views may be reconstructed from the volume data record by employing an interpolation method.

Figure 2:
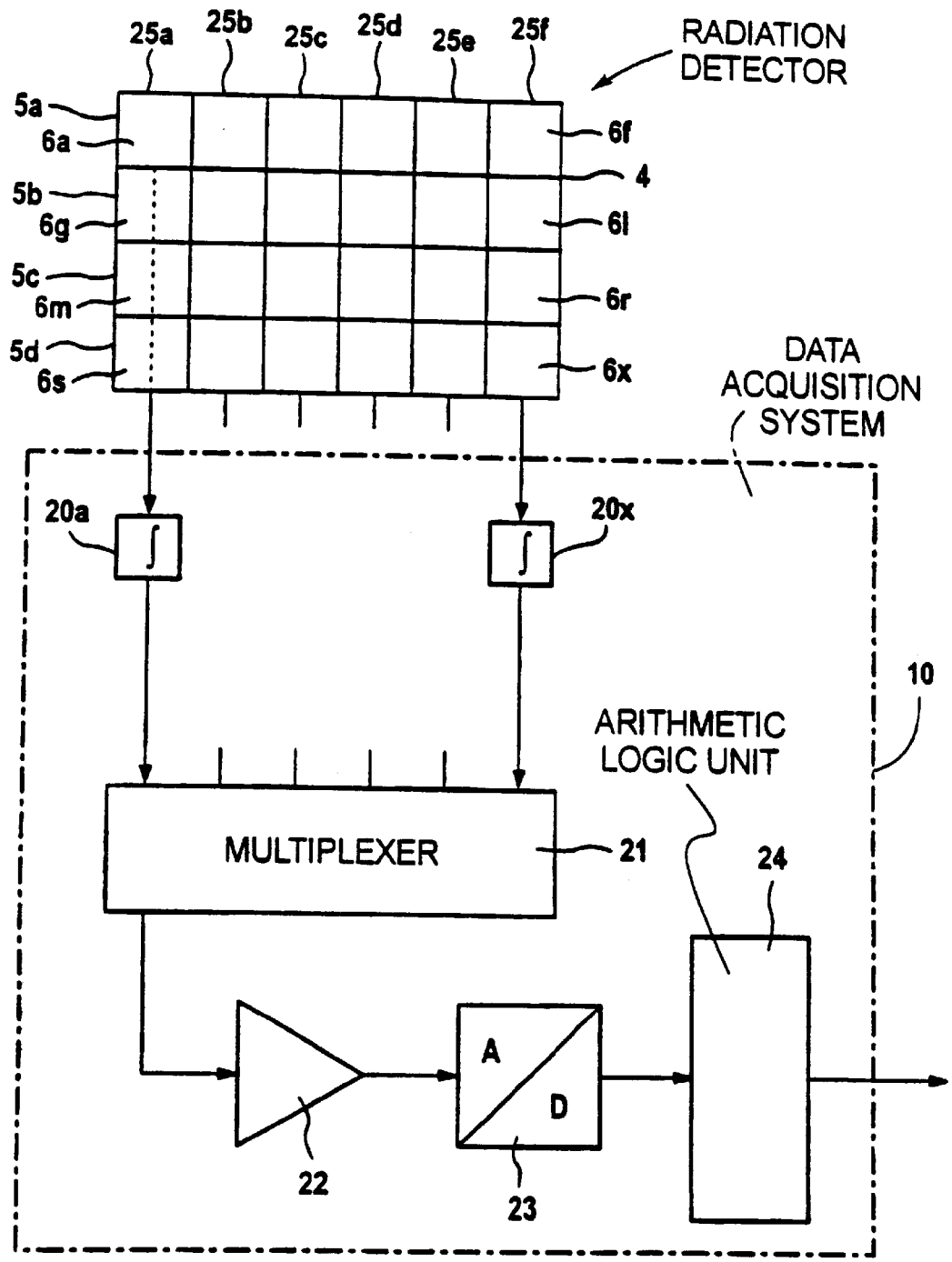
FIG. 2 is a block diagram illustrating the acquisition of difference signals at the digital level in accordance with the invention.

FIG. 2 depicts a block diagram of the data-acquisition system 10 shown in FIG. 1, which, inter alia, forms difference signals from signals read out from said detector elements 6a through 6x of the radiation detector 4 at each scanning step.

In the exemplary embodiment, each detector element 6a through 6x is followed by an integrator 20a through 20x in the form of a capacitor. FIG. 2 shows only integrators 20a and 20x. As a variation of those shown in FIG. 2, the integrators 20a through 20x may also include amplifier stages or be incorporated into the detector elements 6a through 6x to the extent that the detector elements 6a through 6x have an auto-integrating capability.

Charges created in the detector elements 6a through 6x by absorption of X-rays are integrated over a specified time interval by the integrators 20a through 20x for each scanning step and, in the exemplary embodiment, are sequentially read out row by row by a multiplexer 21, and are amplified, by an amplifier 22. Thus signals read out first from detector element 6a, then from detector elements 6b to 6f, then from detector elements 6g to 6l etc. will be sequentially available at the output of said electronic element 22. Alternatively, the detector elements 6a through 6x may be read out column by column.

The signals from the detector elements 6a through 6x that have been read out and amplified by the electronic element 22 are subsequently sequentially digitized by an analog/digital converter 23 and, in the exemplary embodiment, are sent to an arithmetic logic unit (ALU) 24. In the arithmetic logic unit 24, in the case where the detector elements 6a through 6x have been read out row by row, difference signals are formed from signals from pairs of adjacent read-out detector elements 6a through 6x of the linear detector array 5a through 5d, in accordance with the following method:

The signals $S^*_{m,1}$ are formed as $$S^*_{m,1} = S_{m,1}$$

where $$1 \leq m \leq 4.$$

In the exemplary embodiment signal $S_{1,1}$ being the digitized signal read out from the first detector element 6a, $S_{2,1}$ is the digitized signal read out from the second detector element 6g, $S_{3,1}$ is the digitized signal read out from the third detector element 6m, and $S_{4,1}$ is the digitized signal read out from the fourth detector element 6s, of the first detector column 25a of the radiation detector 4. The radiation detector 4 has four linear detector arrays 5a through 5d. The aforementioned signals are present at the output of the ALU 24 in digitized form. $S^*_{m,1}$ are the signals that are available at the output of the ALU 24, and sent to the signal processor 12 shown in FIG. 1.

The difference signals $S^*_{m,k}$, with, in the present exemplary embodiment, $1 < k \leq 6$, are formed as $$S^*_{m,k} = S_{m,k} - S_{m,k-1}.$$

The signals $S_{m,k}$ are the digitized signals read out from the detector elements 6a through 6x of the $m^{th}$ of the four linear detector arrays 5a through 5d (in the exemplary embodiment, 5a is the first of the linear detector arrays, 5b is the second of the linear detector arrays, 5c is the third of the linear detector arrays, and 5d is the fourth of the linear detector arrays) and the $k^{th}$ column of the six detector columns 25a through 25f (in the exemplary embodiment, for example, the first of the detector columns is 25a, the second of the detector columns is 25b, etc.) which are available at the input of the ALU 24 in digitized form. The difference signals $S^*_{m,k}$ ($1 \leq k < 6$) are available at the output of the ALU 24 and are sent to the signal processor 12 shown in FIG. 1.

Since the amplitudes of signals read out from pairs of adjacent detector elements 6a through 6x are highly unlikely to differ by very much, it is highly likely that the rates of change of the difference signals $S^*_{m,k}$ ($1 < k \leq 6$) will be less than those of signals $S_{m,k}$ read out from single detector elements 6a through 6x. Consequently, the difference signals $S^*_{m,k}$ ($1 < k \leq 6$) can be supplied to the signal processor 12 using shorter data lengths than in the case of signals $S_{m,k}$ read out from single detector elements 6a through 6x.

In the exemplary embodiment, the difference signals $S^*_{m,k}$ ($1 < k \leq 6$) are encoded by the ALU 24 using a data length of only one byte, one bit being used to represent the algebraic sign, four bits being used to represent the mantissa, and three bits being used to represent the exponent. The signals $S^*_{m,1}$, i.e. those signals corresponding to the signals read out from detector elements 6a, 6g, 6m, and 6s of said first detector column 25a, are not difference signals and, in the exemplary embodiment, have greater data lengths than the difference signals $S^*_{m,k}$ ($1 < k \leq 6$) while they are being supplied to the signal processor 12. Since at least the difference signals $S^*_{m,k}$ ($1 < k \leq 6$) are supplied from the data-acquisition system 10 to the signal processor 12 with shorter data lengths than the signals corresponding to a detector element 6a through 6x read out, the data rate for transmission from the data-acquisition system 10 to the signal processor 12 is reduced.

Alternatively, instead of the difference signals $S^*_{m,k}$ ($1 < k \leq 6$) of a linear detector array 5a through 5d, difference signals derived from signals read out from pairs of adjacent detector elements 6a through 6x of the detector columns 25a through 25f can be formed. In this alternative difference signals $S^*_{m,k}$ ($1 < m \leq 4$) are formed from signals from the detector elements 6a through 6x of the six detector columns 25a through 25f, in accordance with the following method:

The signals $S^*_{1,k}$ are formed as $$S^*_{1,k} = S_{1,k}$$

where $$1 < k \leq 6,$$

the signals $S_{1,k}$ being the digitized signals read out from the detector elements, 6a through 6f, of the first linear detector array 5a.

The difference signals $S^*_{m,k}$, where, in the case of the present exemplary embodiment, $1 < m \leq 4$, are formed as $$S^*_{m,k} = S_{m,k} - S_{m-1,k}.$$

The statements made above regarding the data lengths of said signals $S^*_{1,k}$ and the difference signals $S^*_{m,k}$ ($1 < m \geq 4$) apply analogously.

Figure 3:
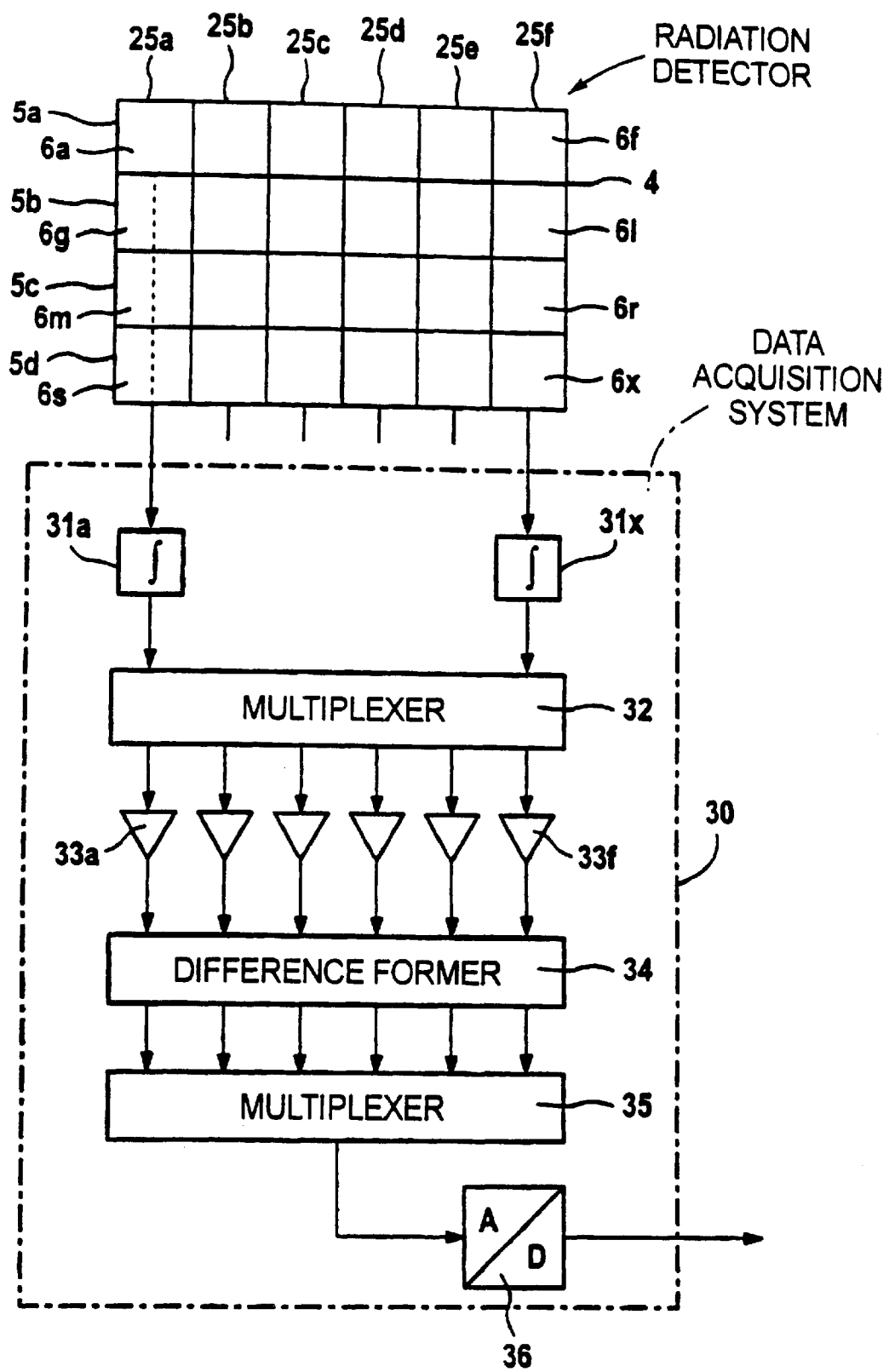
FIGS. 3 and 4 are block diagrams illustrating the acquisition of difference signals at the analog level in accordance with the invention.

The difference signals also can be formed at the analog level. FIG. 3 schematically depicts an exemplary embodiment of a data-acquisition system 30 that, inter alia, forms difference signals at the analog level from the detector elements, 6a through 6x, of said radiation detector 4 of the computed tomography system shown in FIG. 1 read out by the data-acquisition system 30.

In a manner similar to that shown in FIG. 2 and described above, the detector elements 6a through 6x are followed by integrators 31a through 31x. Only the integrators 31a and 31x are depicted in FIG. 3.

Analogously to the case described above, the integrators 31a through 31x integrate the charges created in said detector elements 6a through 6x on absorption of X-radiation over a specified time interval for each scanning step.

In the exemplary embodiment, the outputs of the integrators 31a through 31x are selected row by row using a column multiplexer 32 connected to electronic elements 33a through 33f, i.e. the electronic elements 33a through 33f first read out detector elements 6a through 6f of the first linear detector array 5a in parallel, then read out detector elements 6g through 6l of the second linear detector array 5b in parallel, then read out detector elements 6m through 6r of the third linear detector array 5c in parallel, and finally read out detector elements 6s through 6x of the fourth linear detector array 5d in parallel, and amplify those respective signals.

The output signals from the electronic elements 33a through 33f are sent to a difference former 34 that, inter alia, forms difference signals from signals from pairs of adjacent read-out detector elements 6a through 6x of a detector column 25a through 25f, similarly to the method described above:

Said signals $S^*_{1,k}$ are formed as $$S^*_{1,k} = S_{1,k}$$

where $$1 \leq k \leq 6.$$

In the exemplary embodiment the signals $S_{1,k}$ being read out from the detector elements 6a through 6f of the first linear detector array 5a.

The difference signals $S^*_{m,k}$, with, in the exemplary embodiment, $1<m\leq 4$, are formed as $$S^*_{m,k}=S_{m,k}-S_{m-1,k}.$$

The signals $S^*_{1,k}$ ($1\leq k\leq 6$) and the difference signals $S^*_{2,k}$ ($1\leq k<6$), $S^*_{3,k}$ ($1<k\leq 6$), and $S_{*4,k}$ ($1\leq k\leq 6$), are, in turn, converted by a multiplexer 35 into a serial data stream that is digitized by an analog/digital converter 36, and are thus available at the outputs of the difference former 34, for each scanning step.

Since the difference signals $S^*_{m,k}$ ($1<m\leq 4$), generally have rates of change less than those of the signals $S_{m,k}$ read out from said detector elements 6a through 6x, they can be supplied to the signal processor 12 shown in FIG. 1 using shorter data lengths. Similarly to the data-acquisition device 10 shown in FIG. 2, their data length may be only one byte, where one bit is used for the algebraic sign, four bits are used for the mantissa, and three bits are used for the exponent.

If the detector elements 6a through 6x are alternatively read out column by column, a row multiplexer with appropriate outputs is provided instead of the column multiplexer 32 shown in FIG. 3, in which case the difference former forms difference signals from signals read out from pairs of adjacent detector elements 6a through 6x of a linear detector array 5a through 5d.

Figure 4:
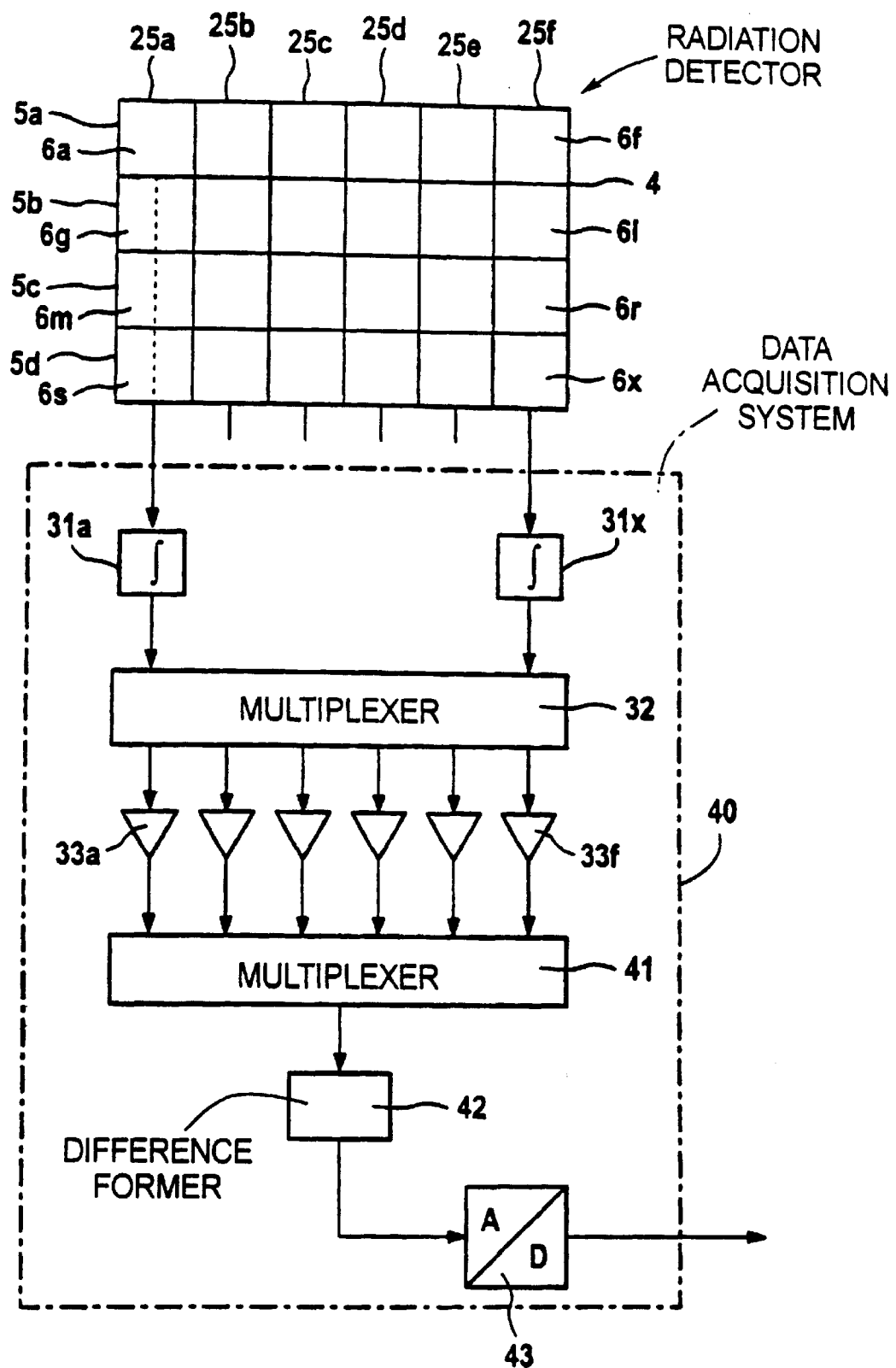

FIG. 4 schematically depicts an alternative data-acquisition system 40 for reading out and forming difference signals at the analog level for the computed tomography system shown in FIG. 1. Unless otherwise stated, the components of the data-acquisition system 40 shown in FIG. 4 that are largely identical in form and function to those of the data-acquisition system 30 that is shown in FIG. 3, and has been described above, have the same reference symbols.

In the data-acquisition system 40 shown in FIG. 4, the electronic elements 33a through 33f that read out the detector elements 6a through 6x are followed by a multiplexer 41 that converts signals from the detector elements 6a through 6x, which are read out row by row, into a sequential data stream, i.e. the signals read out from detector elements 6a, 6b, 6c, through 6x are available, one after the other, at the output of the multiplexer 41, for each scanning step. The signals are sent to a difference former 42 that, as in the method described above, forms difference signals $S^*_{m,k}$ ($1<k\leq 6$) from signals read out from pairs of adjacent detector elements 6a through 6x of the linear detector arrays 5a through 5f. The signal $S^*_{1,1}$, the difference signals $S^*_{1,k}$ ($1<k\leq 6$), the signal $S^*_{2,1}$, the difference signals $S^*_{2,k}$ ($1<k\leq 6$), the signal $S^*_{3,1}$, the difference signals $S^*_{3,k}$ ($1<k\leq 6$), the signal $S^*_{4,1}$ and the difference signals $S_{*4,k}$ ($1<k\leq 6$), that are digitized by an analog/digital converter 43, are thus available, one after the other, at the output of said difference former 42, for each scanning step. The difference signals $S^*_{m,k}$ ($1<k\leq 6$), can be supplied in a manner similar to that in the exemplary embodiments described above using data lengths that are shorter than those for signals read out from a single detector element 6a through 6x.

If the detector elements 6a through 6x are read out column by column, the column multiplexer 32 shown in FIG. 4 is a row multiplexer with appropriate outputs, and the difference former 42 forms difference signals from signals read out from pairs of adjacent detector elements 6a through 6x of a detector column 25a through 25f.

Figure 5:
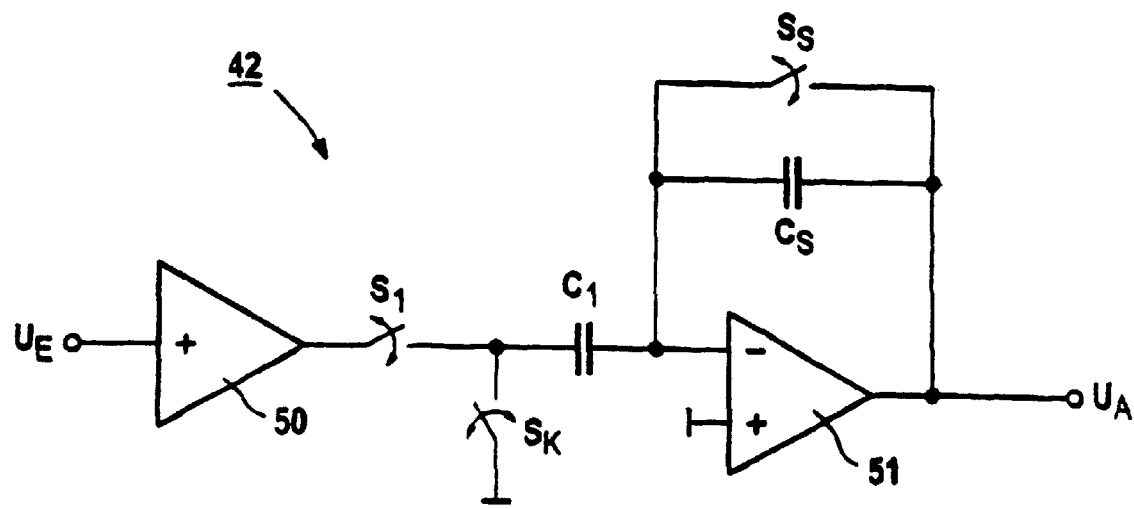
FIG. 5 shows an exemplary embodiment of a circuit for acquiring analog difference signals in accordance with the invention.

FIG. 5 schematically depicts an exemplary embodiment of the analog difference former 42, that forms differences derived from pairs of consecutive signals. In the exemplary embodiment, said difference former 42 has a buffer, 50, which sequentially receives input signals from the read-out detector elements 6a through 6x shown in FIGS. 1 through 4. The output of the buffer 50 may be switched to a coupling capacitor $C_1$ using a switch $S_1$. The coupling capacitor $C_1$ is, in turn, connected to an inverting input of an amplifier stage, for example an operational amplifier 51. In addition, the inverting input of the operational amplifier 51 is connected to the output of the operational amplifier 51 using a sampling capacitor $C_S$ that can be discharged using a switch $S_S$. The coupling capacitor $C_1$ can be discharged using the switch $S_1$ and a switch $S_K$. In addition, the non-inverting input of the operational amplifier 51 is grounded.

Figure 6:
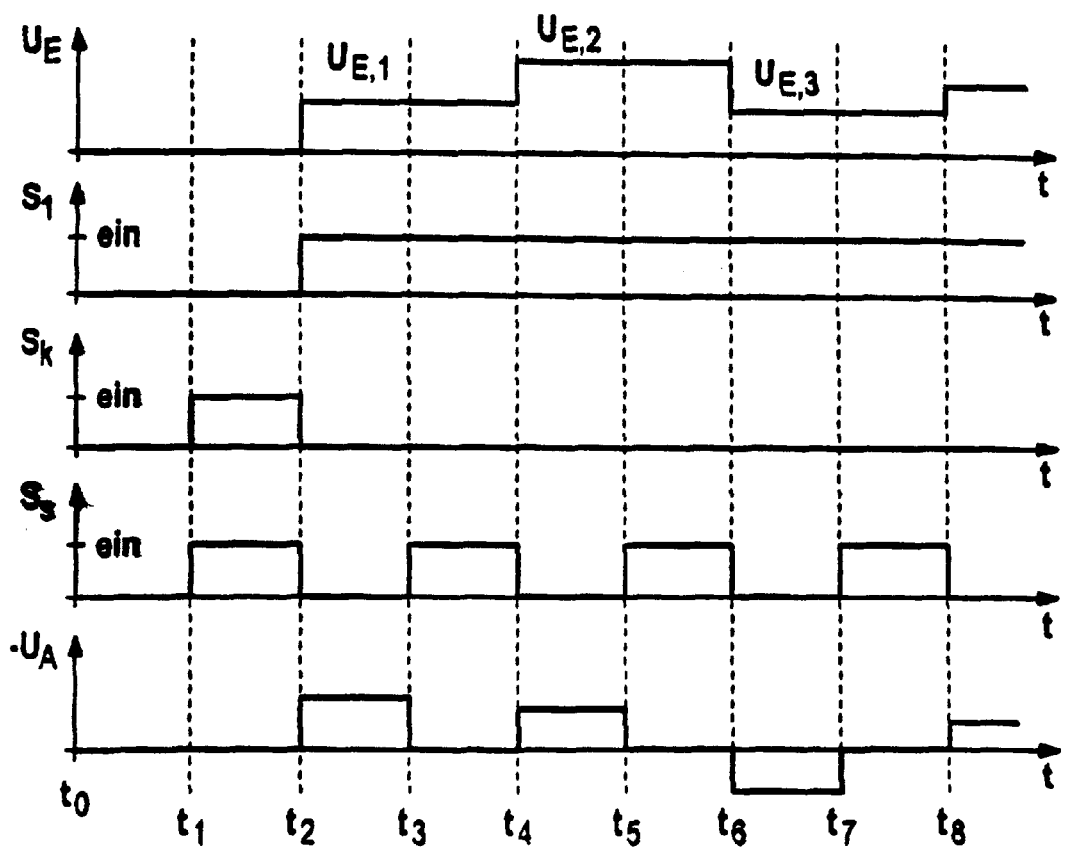
FIG. 6 shows plots for explaining the operation of the circuit illustrated in FIG. 5.

FIG. 6 depicts, schematically and byway of example, sample plots explaining the operation of the difference former 42 shown in FIGS. 4 and 5, which forms difference signals from signals from pairs of adjacent, read-out detector elements 6a through 6x of the linear detector arrays 5a through 5d.

At time $t_0$, there is no input signal ($U_E=0$) at the input of the buffer 50, and the switch $S_1$ is open. At time $t_1$, the sampling capacitor $C_S$ is discharged by the closing of switch $S_S$, and the coupling capacitor $C_1$ is discharged by means of the closed switch $S_K$.

At time $t_2$, the switches $S_K$ and $S_S$ are opened, the switch $S_1$ is closed, and an input signal $U_{E,1}$ is applied to the input of the buffer 50. The signal $U_{A,1}=-U_{E,1}$ is thus present at the output of the operational amplifier 51. The input signal $U_{E,1}$ is, in the exemplary embodiment, the signal $S_{1,1}$ read out from detector element 6a of the radiation detector 4, i.e. the output signal $U_{A,1}=-S_{1,1}$.

At time $t_3$, the switch $S_S$ is closed, discharging the sampling capacitor $C_S$, and there is no signal present at the output of the operational amplifier 51. The coupling capacitor $C_1$ stores the input signal $U_{E,1}$, i.e. $S_{1,1}$.

At time $t_4$, the switch $S_S$ is reopened and an input signal $U_{E,2}$ is applied to the input of the buffer 50. The input signal $U_{E,2}$ is, in the exemplary embodiment, the signal $S_{1,2}$ read out from detector element 6b. Due to the capacitive coupling of the buffer 50 and the operational amplifier 51 using the coupling capacitor $C_1$ the signal present at the output of the operational amplifier 51 is then—$(U_{E,2}-U_{E,1})$, i.e. the output signal $U_{A,2}=-(S_{1,22}-S_{1,1})=-S^*_{1,2}$.

At time $t_5$, the switch $S_S$ is closed again, the sampling capacitor $C_S$ is discharged, and there is, once again, no signal present at the output of the operational amplifier 51. The coupling capacitor $C_1$ then stores the input signal $U_{E,2}$, i.e. $S_{1,2}$.

At time $t_6$, the switch $S_S$ is reopened and an input signal $U_{E,3}$ is applied to the input of the buffer 50, which input signal $U_{E,3}$ is, in the exemplary embodiment, the signal $S_{1,3}$ read out from detector element 6c. The signal present at the output of the operational amplifier 51 is thus $U_{A,3}=-(U_{E,3}-U_{E,2})=-S^*_{1,3}$. The difference former 42 shown in FIG. 5 thus is able to form difference signals derived from consecutive signals present at the input of the buffer 50.

The difference former 42 shown in FIG. 5 also is suitable for forming the difference signals of signals from pairs of adjacent read-out detector elements 6a through 6x of a detector column 25a through 25f.

The difference former 34 shown in FIG. 3 has several inputs and outputs. The difference former 34 may, for example, be designed such that it is formed by a number of difference formers shown in FIG. 5, this number corresponding to the number of inputs and outputs on the difference former 34.

Figure 7:
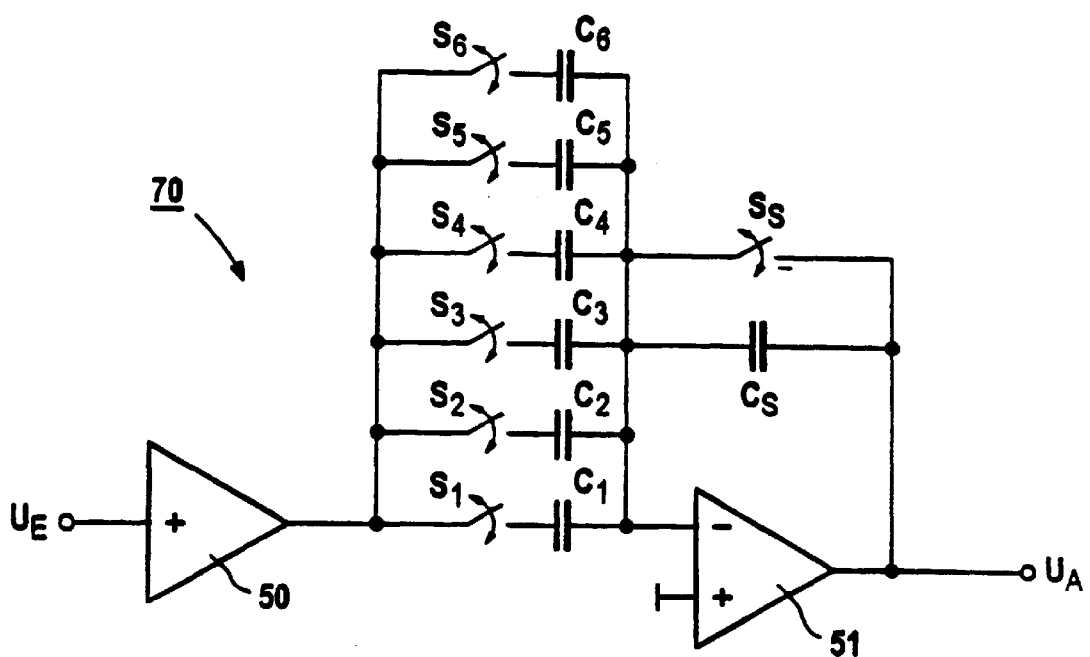
FIG. 7 shows another exemplary embodiment of a circuit for acquiring analog difference signals in accordance with the invention.

FIG. 7 schematically depicts another embodiment of a difference former 70 that is capable of storing several (in the present exemplary embodiment, six) signal values. Unless otherwise stated, components of the difference former 70 shown in FIG. 7 that are largely identical in form and function to those of the difference former 42 that is shown in FIG. 5 and has been described above have the same reference symbols.

As in the case of the difference former 42 shown in FIG. 5, the difference former 70 shown in FIG. 7 has a buffer 50 with an input and receiving signals from the sequentially read detector elements 6a through 6x shown in FIGS. 1 through 4. The output of the buffer 50 may be switched to coupling capacitors $C_1$ through $C_6$ using switches $S_1$ through $S_6$. The coupling capacitors $C_1$ through $C_6$ are, in the exemplary embodiment, in turn connected to an inverting input of an amplifier stage, for example an operational amplifier 51. In addition, the inverting output of the operational amplifier 51 is connected to the output of the operational amplifier 51 using a sampling capacitor $C_S$. The sampling capacitor $C_S$ may be discharged using a switch $S_S$. In addition, the non-inverting input of the operational amplifier 51 is grounded. For clarity, the switches for discharging the coupling capacitors $C_1$ through $C_6$ are not shown in FIG. 7.

In the exemplary embodiment, said difference former 70 shown in FIG. 7 may be used instead of the difference former 42 shown in FIG. 4. At the input to the difference former 70, there are signals $S_{m,k}$ that have been read out in sequence, row by row, from the detector elements 6a through 6x. Since the difference former 70 has six coupling capacitors $C_1$ through $C_6$, six signals can be stored. In particular, for each scanning step, those signals $S_{1,k}$, read out from the detector elements 6a through 6f of the first linear detector array 5a, may be stored first, followed by those signals $S_{2,k}$ read out from the detector elements 6g through 6l of the second linear detector array 5b. The switches $S_1$ through $S_6$ are cyclically closed and reopened so that signals from the detector elements 6a through 6x of the linear detector array 5a through 5d can be read out one after the other and respectively stored in one of the coupling capacitors $C_1$ through $C_6$.

Figure 8:
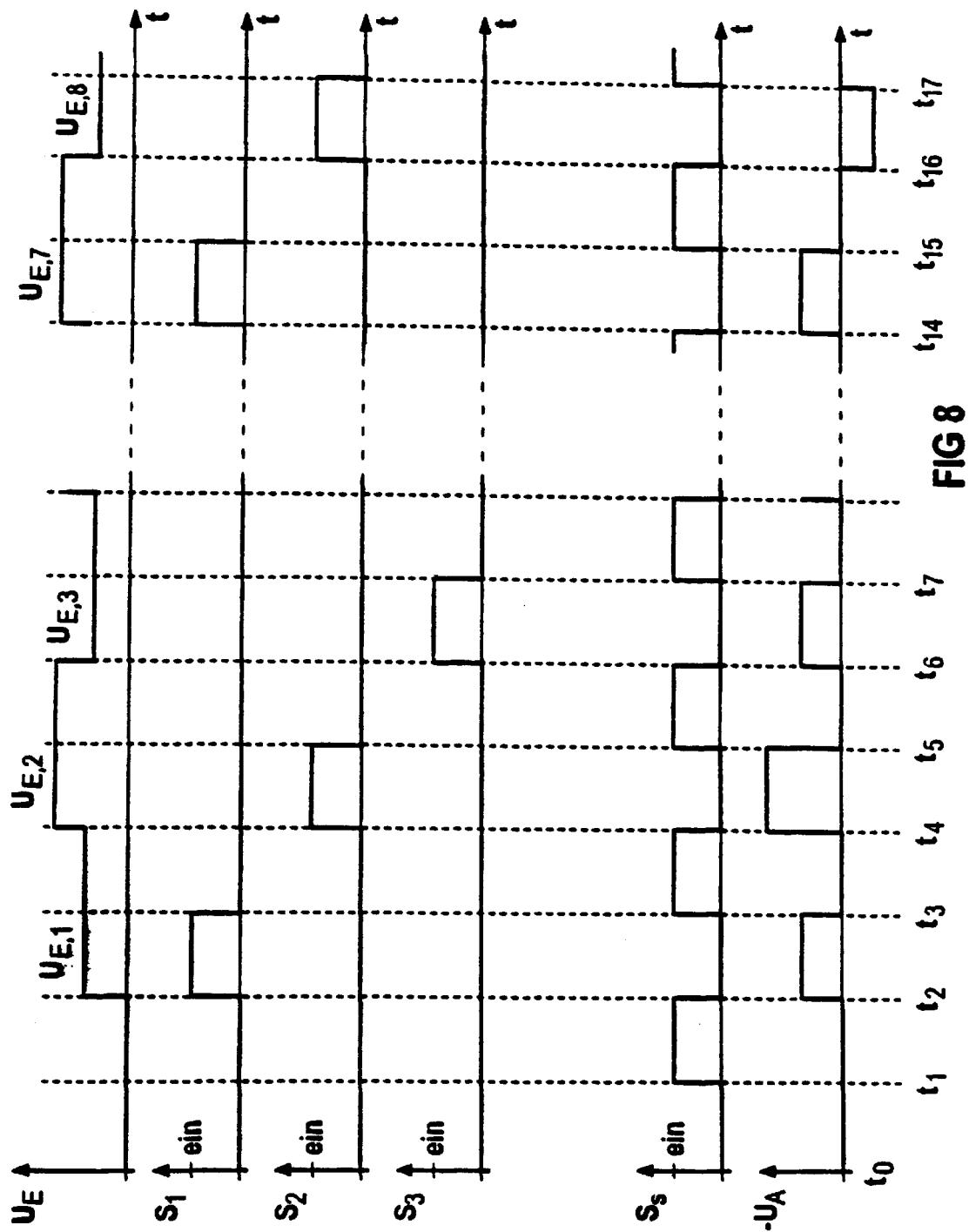
FIG. 8 shows plots for explaining the operation of the circuit illustrated in FIG. 7.

FIG. 8 depicts, schematically and by way of example, sample plots explaining the operation of the difference former 70 shown in FIG. 7, to which signals from said read-out detector elements 6a through 6x are applied sequentially and row by row.

At time $t_0$, there is no input signal ($U_E$=0) at the input of the buffer 50, and the switches $S_1$ through $S_6$ are open. At time $t_1$, the sampling capacitor $C_S$ is discharged by the closing of switch $S_S$ and the coupling capacitors $C_1$ through $C_6$ are discharged by means of switches that are not shown.

At time $t_2$, the switch $S_S$ is opened, the switch $S_1$ is closed, and an input signal $U_{E,1}$ is applied to the input of the buffer 50. The signal $U_{A,1}$=$-U_{E,1}$ thus is present at the output of the operational amplifier 51. The input signal $U_{E,1}$ is, in the exemplary embodiment, the signal $S_{1,1}$ read out from detector element 6a of the radiation detector 4, i.e. the output signal $U_{A,1}$=$-S_{1,1}$.

At time $t_3$, the switch $S_S$ closed, the switch $S_1$ is opened, the sampling capacitor $C_S$ is discharged, and there is no signal at the output of the operational amplifier 51. The coupling capacitor $C_1$ therefore stores the input signal $U_{E,1}$, i.e. the signal $S_{1,1}$.

At time $t_4$, the switch $S_S$ is reopened, the switch $S_2$ is closed, and an input signal $U_{E,2}$ is applied to the input of the buffer 50. The input signal $U_{E,2}$ is, in the exemplary embodiment, the signal $S_{1,2}$ read out from detector element 6b. The signal at the output of the operational amplifier 51 thus is the signal $U_{A,2}$=$-S^*_{1,2}$.

At time $t_5$, the switch $S_S$ is closed again, the switch $S_2$ is opened, the sampling capacitor $C_S$ is discharged, and there is, once again, no signal at the output of the operational amplifier 51. The coupling capacitor $C_2$ then stores the input signal $U_{E,2}$, i.e. signal $S_{1,2}$.

At time $t_6$, the switch $S_S$ is reopened, the switch $S_3$ is closed, and an input signal $U_{E,3}$ is applied to the input of the buffer 50. The input signal $U_{E,3}$ is, in the exemplary embodiment, the signal $S_{1,3}$ read out from detector element 6c. The signal at the output of the operational amplifier 51 thus is the signal $U_{A,3}$=$-S_{1,3}$.

At time $t_7$, the switch $S_S$ is closed again, the switch $S_3$ is opened, the sampling capacitor $C_S$ is discharged, and there is, once again, no signal at the output of the operational amplifier 51. The coupling capacitor $C_3$ then stores the input signal $U_{E,3}$, i.e. signal $S_{1,3}$.

At times $t_8$ through $t_{13}$, which are not shown in FIG. 8, the input signals $U_{E,4}$ through $U_{E,6}$, which correspond to the signals $S_{1,4}$ through $S_{1,6}$ read out from detector elements 6d through 6f, are applied one after another to the input of the buffer 50. The signals at the output of the operational amplifier 51 are correspondingly the signals $U_{A,4}$=$-S_{1,4}$ through $U_{A,6}$=$-S_{1,6}$, and the coupling capacitor $C_4$ stores the signal $S_{1,4}$, the coupling capacitor $C_5$ stores the signal $S_{1,5}$, and the coupling capacitor $C_6$ stores the signal $S_{1,6}$.

At time $t_{14}$, the switch $S_S$ is reopened, the switch $S_1$ is closed again, and an input signal $U_{E,7}$ is applied to the input of the buffer 50, the input signal $U_{E,7}$ is, in the exemplary embodiment, the signal $S_{2,1}$ read out from detector element 6g of the second linear detector array 5b.

Due to the capacitive coupling of the buffer 50 and the operational amplifier 51 using the coupling capacitor $C_1$, the signal at the output from the operational amplifier 51 is then—$(U_{E,7}-U_{E,1})$, i.e. the output signal $U_{A,2}$=$-(S_{2,1}-S_{1,1})$=$-S^*_{2,1}$, a difference signal between those signals read out from the pair of read-out adjacent detector elements 6a and 6g of detector column 25a.

At time $t_{15}$, the switch $S_S$ is closed again, the switch $S_1$ is reopened, the sampling capacitor $C_S$ is discharged, and there is, once again, no signal at the output of the operational amplifier 51. Said coupling capacitor $C_3$ then stores the input signal $U_{E,7}$, i.e. the signal $S_{2,1}$.

At time $t_{16}$, the switch $S_S$ is reopened, the switch $S_2$ is closed again, and an input signal $U_{E,8}$ is applied to the input of the buffer 50. The input signal $U_{E,8}$, in the exemplary embodiment, is the signal $S_{2,2}$ read out from detector element 6h of the second linear detector array 5b. The signal at the output from the operational amplifier 51 thus is the difference signal $U_{A,8}$=$-(U_{E,3}-U_{E,8})$=$-S^*_{2,2}$. The difference former 42 shown in FIG. 5 thus, in the exemplary embodiment, is able to form the difference signals between signals from pairs of adjacent read-out detector elements 6a through 6x of a detector column 25a through 25f.

If an appropriate number of coupling capacitors is employed and the input signals are suitable, the difference former 70 shown in FIG. 7 also is suitable for forming the difference signals between signals from pairs of adjacent read-out detector elements 6a through 6x of the linear detector array 5a through 5d.

The difference former 34 shown in FIG. 3 has several inputs and outputs. The difference former 34, for example, can be designed such that it is formed of a number of difference formers shown in FIG. 7, the number corresponding to the number of inputs and outputs.

The radiation detector 4 shown in FIGS. 1 through 4 may have more or fewer detector elements than the detector elements 6a through 6x shown in FIGS. 1 through 4, and/or more or fewer linear detector arrays than the linear detector arrays 5a through 5d, and/or more or fewer detector columns than the detector columns 25a through 25f.

It is also possible to employ a radiation detector with several detector modules having at least one linear detector array, each detector module being assigned an analog/digital converter. The difference signals may then be acquired, in accordance with the above-described methods, column by column and/or row by row for each detector module.

It is also possible to form higher-order difference signals, these being understood to be, for example, row-by-row difference signals of difference signals from pairs of adjacent read-out detector elements of a detector column.

The methods described above also may be employed in computed tomography systems equipped with a radiation detector formed by a single-line radiation detector, in which case the difference signals involved will be formed from signals read out from adjacent detector elements of the single-line radiation detector.

The data length of one byte for the difference signals should also be understood as being merely an example.

The object to be investigated need not necessarily be a human patient, as suggested in FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:
    a radiation source which emits an x-ray beam, and a radiation detector on which said X-ray beam is incident after penetrating a subject;
    said radiation detector comprising at least one linear detector array comprising a row of a plurality of detector elements aligned adjacent to one another, the respective detector elements emitting electrical signals dependent on X-rays incident thereon; and
    a data acquisition system connected to said radiation detector for reading out the respective signals from pairs of adjacent detector elements in said row and forming respective difference signals from said pairs of signals, and further processing said difference signals.

2. A computed tomography apparatus as claimed in claim 1 wherein the respective signals emitted by said detector elements are analog signals, and wherein said data acquisition system comprises at least one analog-to-digital converter which digitizes said analog signals.

3. A computed tomography apparatus as claimed in claim 1 wherein said difference signals, as a result of the respective signals emitted by said detector elements being digitized, also are digital, and wherein said digital difference signals each have a data length of one byte.

4. A computed tomography apparatus as claimed in claim 1 wherein the respective signals emitted by said detector elements are analog signals, and wherein said data acquisition system comprises at least one analog-to-digital converter for digitizing said difference signals.

5. A computed tomography apparatus as claimed in claim 4 wherein said digitized difference signals each have a data length of one byte.

6. A computed tomography apparatus as claimed in claim 1 wherein said radiation detector comprises a plurality of detector modules, each of said detector modules comprising a plurality of linear detector arrays, each comprising a plurality of said detector elements aligned adjacent to each other, and wherein said data acquisition system comprises a plurality of analog-to-digital converters respectively connected to said plurality of detector modules for digitizing the respective signals emitted by said detector elements.

7. A method for acquiring signals from a computed tomography apparatus comprising the steps of:
    conducting a scan of a subject in a plurality of scanning steps by irradiating said subject with X-rays from an X-ray source and detecting X-rays after penetrating said subject with a radiation detector having at least one detector module comprising at least one linear detector array with a plurality of detector elements aligned adjacent to one another;
    reading out respective signals from each of said detector elements of a detector module at each scanning step with a data acquisition system; and
    forming signals $S^*_{j,m,k}$ in said data acquisition system from signals read from detector elements of a $j^{th}$ detector module, wherein $S^*_{j,m,1}=S_{j,m,1}$ for k=1 and $S^*_{j,m,k}=S_{j,m,k}-S_{j,m,k-1}$ for $1<k\leq K$, wherein $S_{j,m,k}$ is the signal read out from the $k^{th}$ detector element of $m^{th}$ linear detector array of the $j^{th}$ detector module, and wherein K is the number of detector elements in said $m^{th}$ linear detector array.

8. A method as claimed in claim 7 wherein said signals $S_{j,m,k}$ are analog signals, and comprising the additional step of digitizing said signals $S_{j,m,k}$ and further processing said signals $S_{j,m,k}$ in digital form.

9. A method as claimed in claim 8 wherein said signals $S^*_{j,m,k}$, as a result of said signals $S_{j,m,k}$ being digitized, also are digital, and wherein said signals $S^*_{j,m,k}$ each have a data length of 1 byte.

10. A method as claimed in claim 7 wherein said signals $S^*_{j,m,k}$ are analog signals, and comprising the additional step of digitizing said signals $S^*_{j,m,k}$, and further processing said signals $S^*_{j,m,k}$ in digital form.

11. A method as claimed in claim 10 wherein said digital signals $S^*_{j,m,k}$ each have a data length of 1 byte.

12. A method for acquiring signals from a computed tomography apparatus comprising the steps of:
    conducting a scan of a subject in a plurality of scanning steps by irradiating said subject with X-rays from an X-ray source and detecting X-rays after penetrating said subject with a radiation detector having at least one detector module comprising at least one detector column with a plurality of detector elements aligned adjacent to one another;
    reading out respective signals from each of said detector elements of a detector module at each scanning step with a data acquisition system; and
    forming signals $S^*_{j,m,k}$ in said data acquisition system from signals read from detector elements of a $j^{th}$ detector module, wherein $S^*_{j,1,k}=S_{j,1,k}$ for m=1 and $S^*_{j,m,k}=S_{j,m,k}-S_{j,m-1,k}$ for $1<m\leq M$, wherein $S_{j,m,k}$ is the signal read out from the $m^{th}$ detector element of $k^{th}$ detector column of the $j^{th}$ detector module, and wherein M is the number of detector elements in said $k^{th}$ detector column.

13. A method as claimed in claim 12 wherein said signals $S_{j,m,k}$ are analog signals, and comprising the additional step of digitizing said signals $S_{j,m,k}$ and further processing said signals $S_{j,m,k}$ in digital form.

14. A method as claimed in claim 13 wherein said signals $S^*_{j,m,k}$, as a result of said signals $S_{j,m,k}$ being digitized, also are digital, and wherein said signals $S^*_{j,m,k}$ each have a data length of 1 byte.

15. A method as claimed in claim 12 wherein said signals $S^*_{j,m,k}$ are analog signals, and comprising the additional step of digitizing said signals $S^*_{j,m,k}$, and further processing said signals $S^*_{j,m,k}$ in digital form.

16. A method as claimed in claim 15 wherein said digital signals $S^*_{j,m,k}$ each have a data length of 1 byte.

* * * * *